(12) United States Patent
Kohashi et al.

(10) Patent No.: US 11,756,763 B2
(45) Date of Patent: Sep. 12, 2023

(54) SCANNING ELECTRON MICROSCOPE

(71) Applicant: Hitachi High-Tech Corporation, Tokyo (JP)

(72) Inventors: Teruo Kohashi, Tokyo (JP); Hideo Morishita, Tokyo (JP); Junichi Katane, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 90 days.

(21) Appl. No.: 17/616,253

(22) PCT Filed: Jun. 6, 2019

(86) PCT No.: PCT/JP2019/022452
§ 371 (c)(1),
(2) Date: Dec. 3, 2021

(87) PCT Pub. No.: WO2020/245962
PCT Pub. Date: Dec. 10, 2020

(65) Prior Publication Data
US 2022/0246393 A1 Aug. 4, 2022

(51) Int. Cl.
H01J 37/244 (2006.01)
G01N 23/2251 (2018.01)
H01J 37/28 (2006.01)

(52) U.S. Cl.
CPC ........ *H01J 37/244* (2013.01); *G01N 23/2251* (2013.01); *H01J 37/28* (2013.01);
(Continued)

(58) Field of Classification Search
CPC .. H01J 37/244; H01J 37/28; H01J 2237/2448; H01J 2237/24585;
(Continued)

(56) References Cited

U.S. PATENT DOCUMENTS 8,022,364 B2 * 9/2011 Kohashi ............... G01R 33/093
250/311
8,048,492 B2 * 11/2011 Fukuzawa ............ G11B 5/3983
427/535
(Continued)

FOREIGN PATENT DOCUMENTS

JP H1020044 A 1/1998
JP 2008269967 A 11/2008
(Continued)

OTHER PUBLICATIONS

Search Report dated Sep. 3, 2019 in International Application No. PCT/JP2019/022452.
(Continued)

Primary Examiner — David A Vanore
(74) Attorney, Agent, or Firm — MILES & STOCKBRIDGE, P.C.

(57) ABSTRACT

A scanning electron microscope includes a spin detector configured to measure secondary electron spin polarization of secondary electrons emitted from the sample, and an analysis device configured to analyze secondary electron spin polarization data measured by the spin detector. The analysis device evaluates the strain in the sample by calculating a difference in the secondary electron spin polarization data of adjacent pixels.

13 Claims, 7 Drawing Sheets

(52) U.S. Cl.
CPC ............. *H01J 2237/2448* (2013.01); *H01J 2237/24585* (2013.01); *H01J 2237/2806* (2013.01); *H01J 2237/2813* (2013.01)

(58) Field of Classification Search
CPC ....... H01J 2237/2806; H01J 2237/2813; H01J 2237/24557; G01N 23/2251; G01N 33/204; G01N 2223/607; G01N 2223/624
See application file for complete search history.

(56) References Cited

U.S. PATENT DOCUMENTS

| | | | | |
|---|---|---|---|---|
| 9,881,767 | B2* | 1/2018 | Kuwahara | G01N 23/20 |
| 10,395,885 | B2* | 8/2019 | Kohashi | H01J 37/147 |
| 11,170,972 | B2* | 11/2021 | Kohashi | H01J 37/28 |
| 11,251,011 | B2* | 2/2022 | Ohshima | H01J 37/22 |
| 2007/0194230 | A1* | 8/2007 | Kohashi | H01J 37/29 |
| | | | | 250/310 |
| 2008/0217533 | A1* | 9/2008 | Kohashi | G01N 23/2251 |
| | | | | 324/319 |
| 2010/0155598 | A1* | 6/2010 | Kohashi | G01R 33/093 |
| | | | | 250/311 |
| 2013/0009058 | A1* | 1/2013 | Tanaka | H01J 37/073 |
| | | | | 250/311 |
| 2020/0402762 | A1* | 12/2020 | Kohashi | H01J 37/28 |
| 2022/0246393 | A1* | 8/2022 | Kohashi | H01J 37/28 |

FOREIGN PATENT DOCUMENTS

| | | |
|---|---|---|
| JP | 2010151455 A | 7/2010 |
| JP | 2011059057 A | 3/2011 |
| JP | 201195150 A | 5/2011 |
| WO | 2011122171 A1 | 10/2011 |

OTHER PUBLICATIONS

Written Opinion dated Sep. 3, 2019 in International Application No. PCT/JP2019/022452.

* cited by examiner

[FIG. 1A]
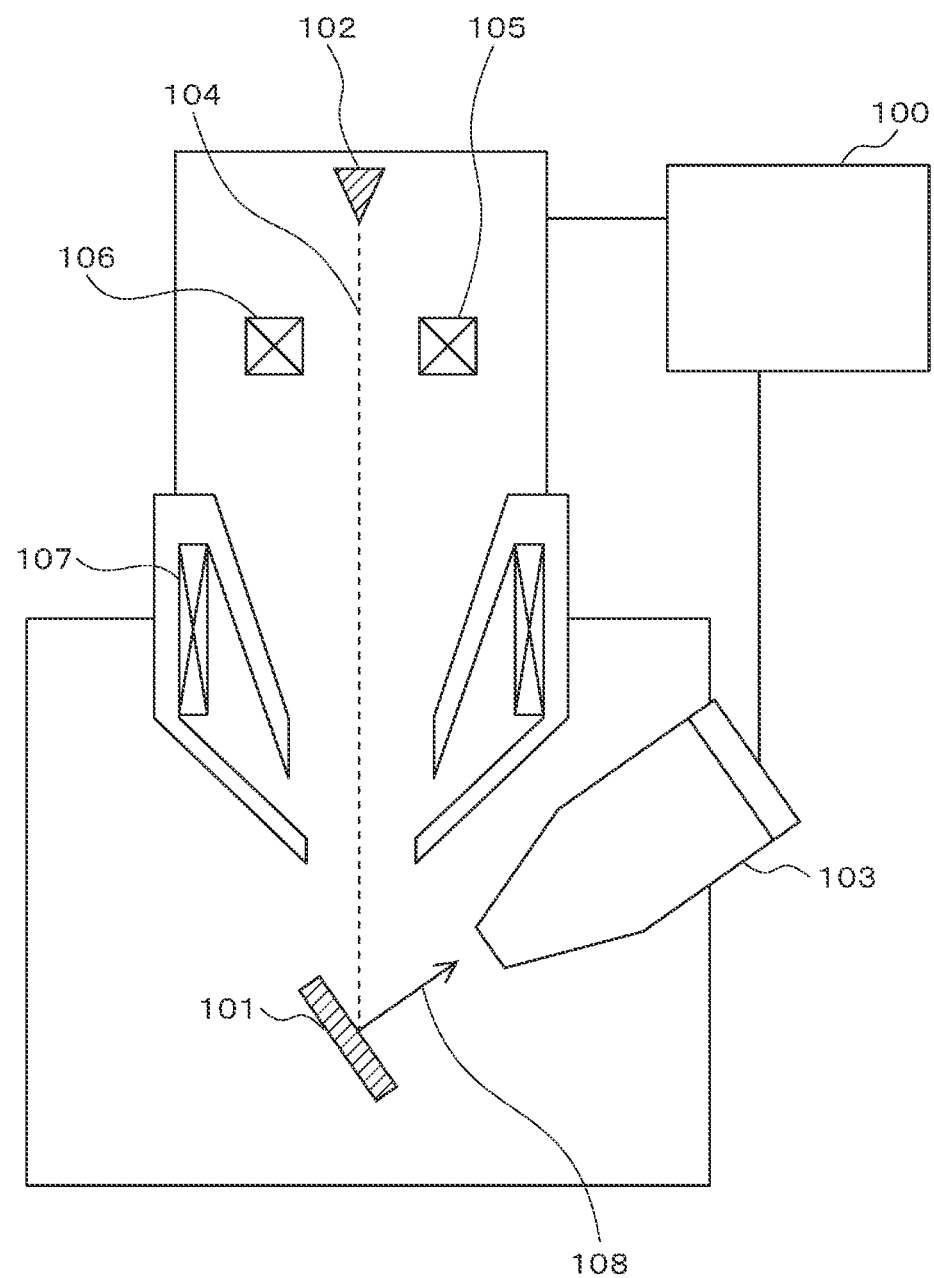

[FIG. 1B]
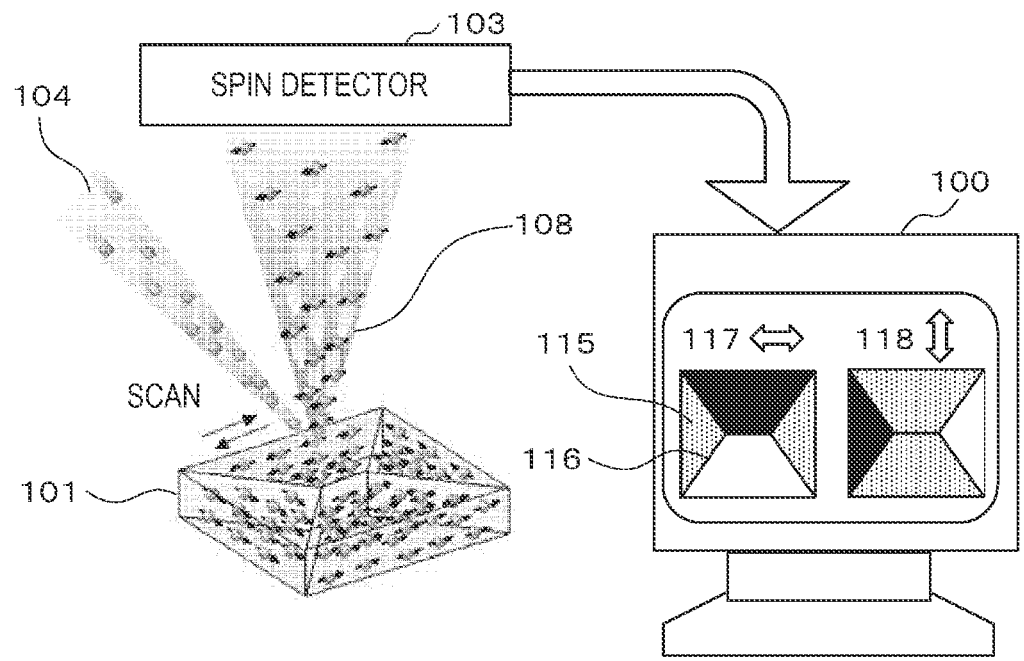
[FIG. 1C]
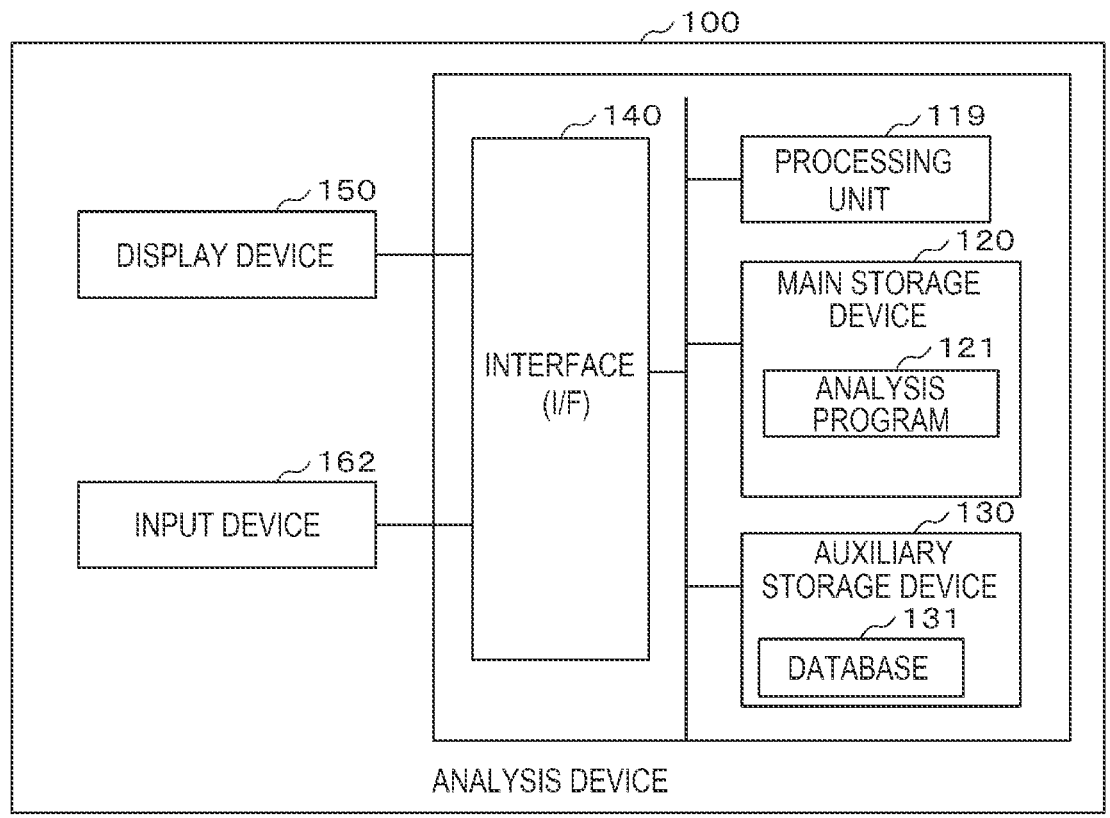

[FIG. 2A]
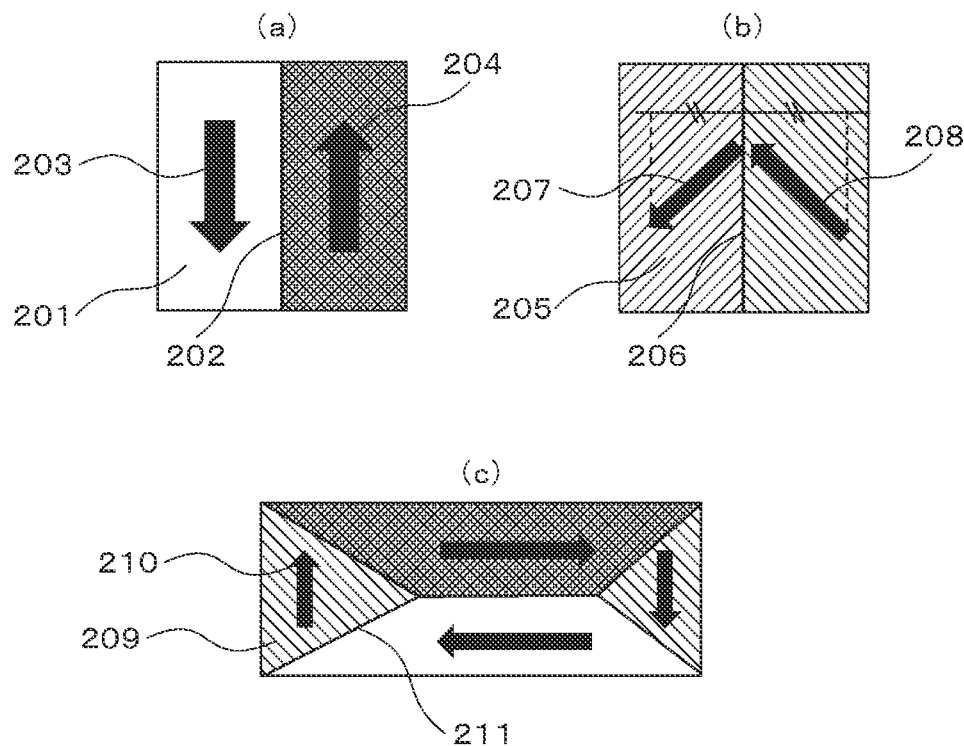
[FIG. 2B]
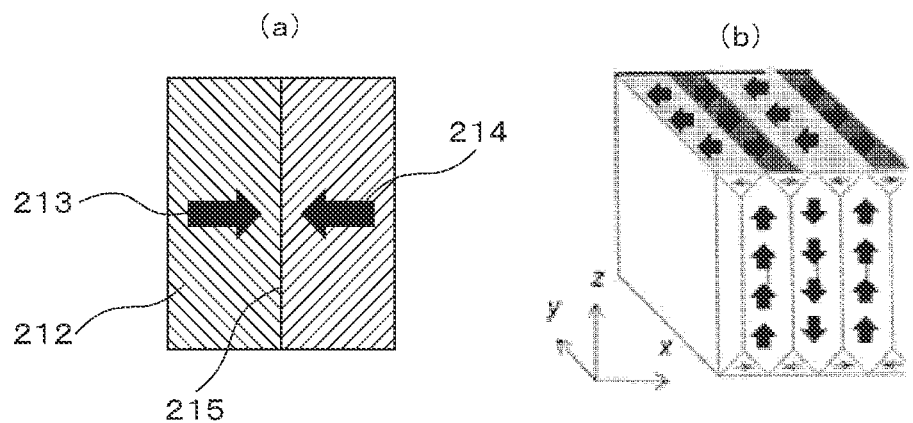

[FIG. 3A]
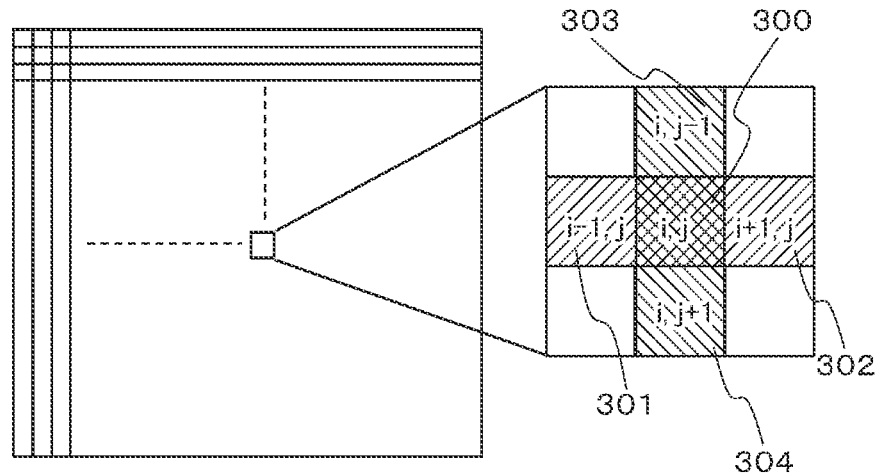
[FIG. 3B]
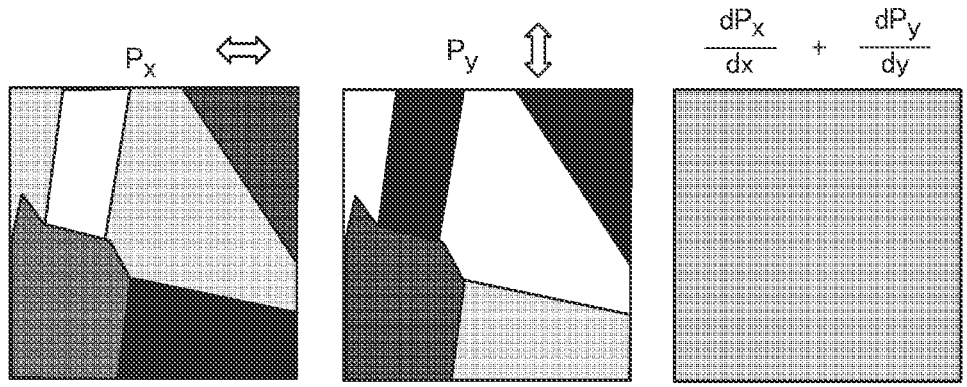
[FIG. 3C]
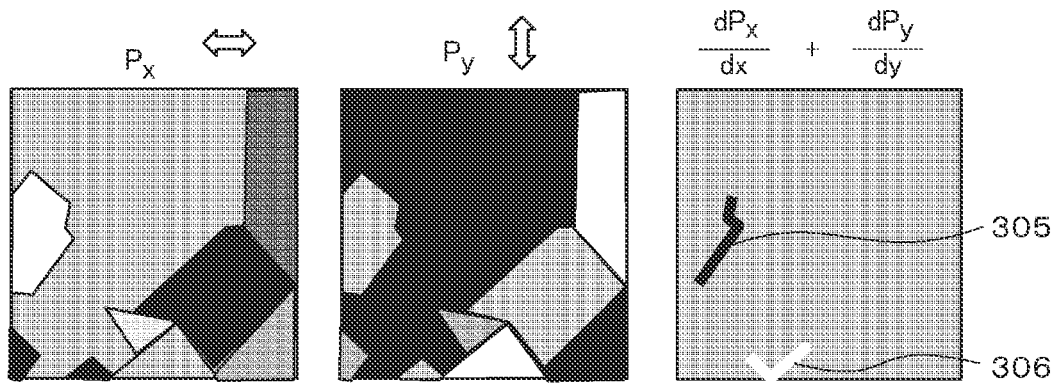

[FIG. 4]
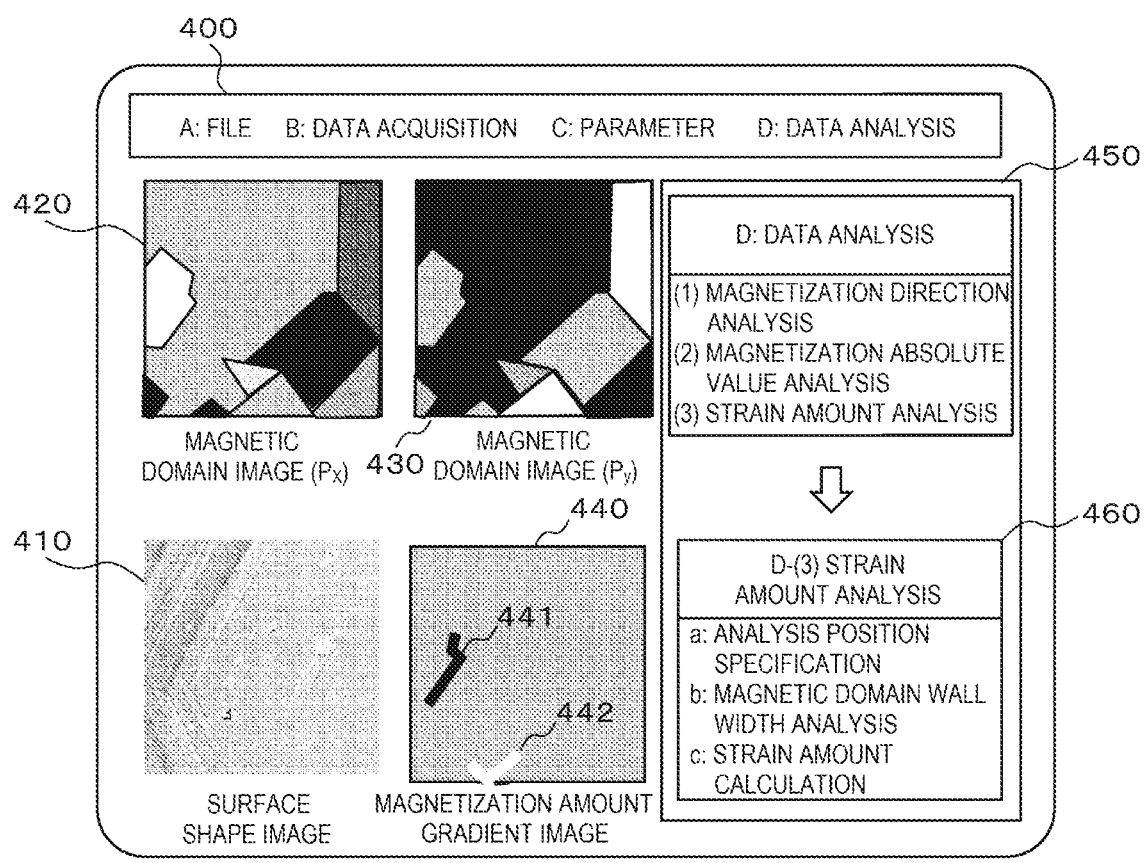

[FIG. 5]
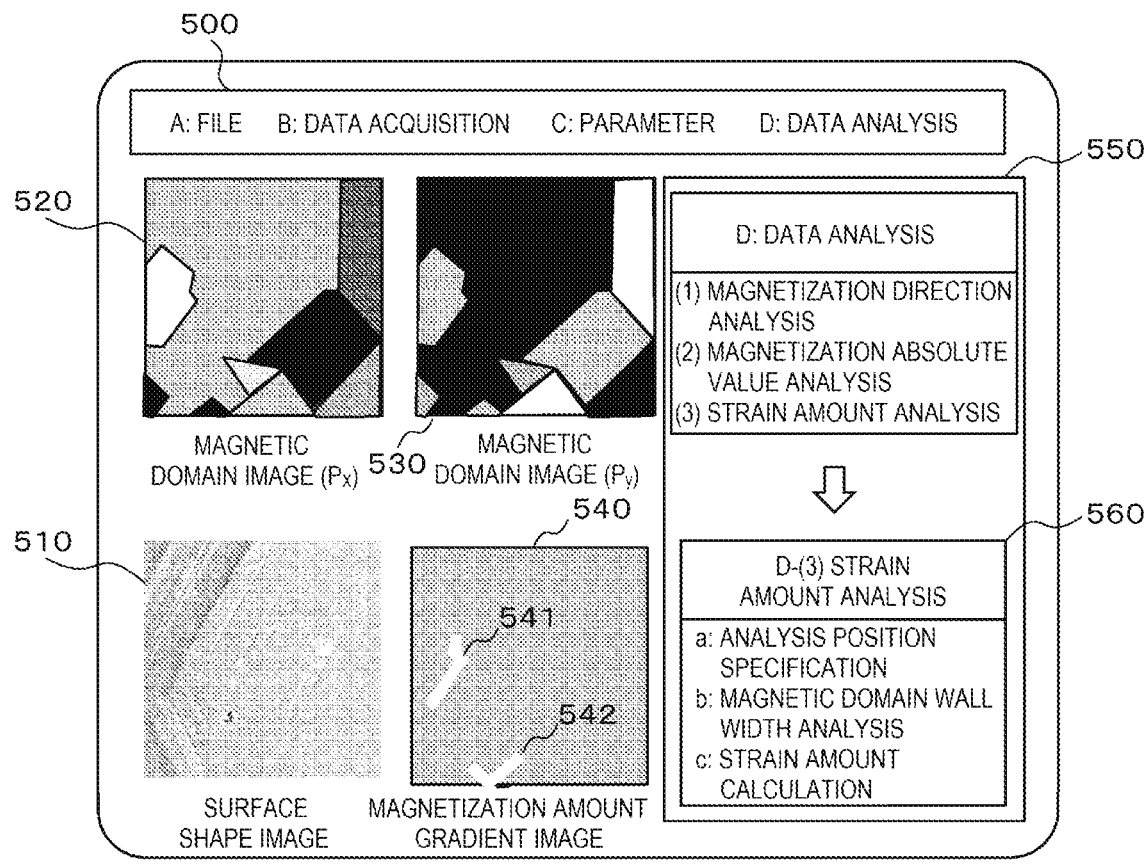
[FIG. 6A]
| POSITION OF SCANNING ELECTRON BEAM | X COMPONENT ($P_x$) | Y COMPONENT ($P_y$) | $dP_x/dx + dP_y/dy$ |
|---|---|---|---|
| x=i, y=j | CALCULATE $P_x(i, j) - P_x(i-1, j)$ | CALCULATE $P_y(i, j) - P_y(i, j-1)$ | CALCULATE SUM OF LEFT TWO COLUMNS |
CONDITIONS OF m, n WHEN ACQUIRING TWO-DIMENSIONAL IMAGE OF m × n PIXELS
$2 \leq i \leq m$
$2 \leq j \leq n$

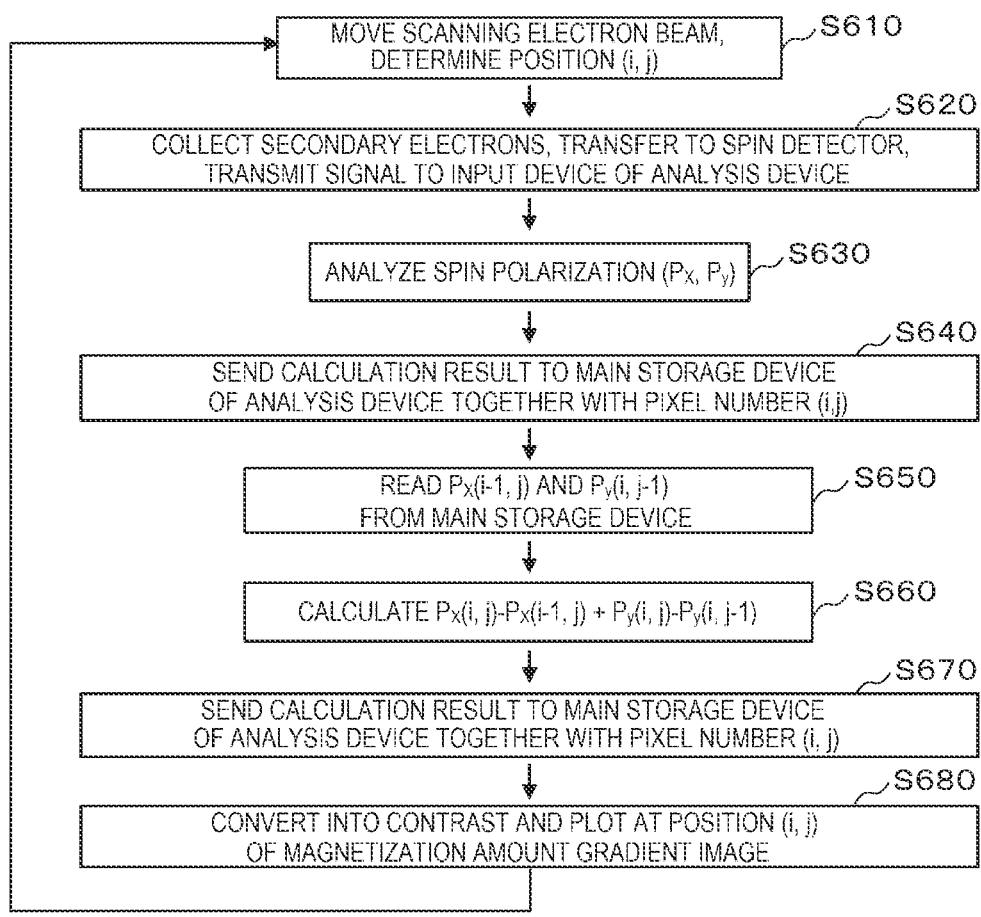

SCANNING ELECTRON MICROSCOPE

TECHNICAL FIELD

The present invention relates to a scanning electron microscope.

BACKGROUND ART

In a scanning electron microscope, there is a method for detecting a spin polarization of secondary electrons from a magnetic material that is a sample and performing magnetization mapping (for example, see PTL 1). It is known that an origin of magnetization is the spin polarization of electrons in a material, and the spin polarization is substantially maintained even when electrons are emitted to an outside of the sample as secondary electrons.

Therefore, when the secondary electrons are transferred to a spin detector and the spin polarization is measured, the magnetization at a secondary electron emission point can be evaluated. Then, when a sample surface is scanned with a primary electron beam and the spin polarization of secondary electrons is sequentially measured, magnetization mapping within a scanning range becomes possible.

This technique is known as a spin polarization scanning electron microscope (spin SEM), and has features such as a high resolution of 10 nm level and a capability of three-dimensionally detecting all magnetization directions. The technique has been utilized in evaluation of magnetic devices, such as magnetic recording materials and permanent magnet materials, and in the field of basic magnetism.

CITATION LIST

Patent Literature

PTL 1: JP-A-2011-059057

SUMMARY OF INVENTION

Technical Problem

It is known that a strain present in a steel material have a large influence on characteristics of the material. For example, deterioration is caused by the strain in a structural material, and anisotropy and magnetic permeability of magnetization are changed in a magnetic material.

These are related directly to the life of the structural material and a power consumption of a motor, and the control of the strain and the measurement thereof are fairly important for the above-described material development. However, on the other hand, an evaluation of a distribution state of the strain is not easy.

Currently, there is a method (KAM method: Kernel Average Misorientation method) for measuring a change in a lattice constant and an orientation difference by an electron backscatter diffraction (EBSD) method, and a current strain amount of about 0.01% is a detection limit. Further, many steel materials have magnetism since a main component of the steel materials is iron. In particular, in an electromagnetic steel sheet or the like, an attempt has been made to obtain information on a strain by magnetic domain observation.

Since a size and a shape of a magnetic domain change due to the strain, the strain is evaluated by a Kerr effect microscope or the like, which is a magnetic domain observation device using an optical microscope. However, even in this method, the observation itself is difficult with respect to the magnetic domain of 1 micron or less due to a problem of resolution. As a performance of the steel materials is improved, evaluation of the strain in more detailed and versatile materials are required. Therefore, a method for evaluating strain with high accuracy is desired.

An object of the invention is to evaluate a strain with high accuracy in a scanning electron microscope.

Solution to Problem

A scanning electron microscope for evaluating a strain in a sample according to one aspect of the invention includes: a spin detector configured to measure secondary electron spin polarization of secondary electrons emitted from the sample; and an analysis device configured to analyze secondary electron spin polarization data measured by the spin detector, in which the analysis device evaluates the strain in the sample by calculating a difference in the secondary electron spin polarization data of adjacent pixels.

A scanning electron microscope for evaluating strain in a sample according to another aspect of the invention includes: a spin detector configured to measure secondary electron spin polarization of secondary electrons emitted from the sample; and an analysis device configured to analyze secondary electron spin polarization data measured by the spin detector, in which the analysis device detects at least two orthogonal components of the secondary electron spin polarization, and evaluates the strain in the sample by calculating a differential value in each component.

Advantageous Effects of Invention

According to the one aspect of the invention, the strain can be evaluated with high accuracy in the scanning electron microscope.

BRIEF DESCRIPTION OF DRAWINGS

FIG. 1A is a schematic diagram showing a basic configuration of a scanning electron microscope.

FIG. 1B is a schematic diagram showing a principle of acquiring a magnetic domain image in the scanning electron microscope.

FIG. 1C is a diagram showing a configuration of an analysis device of the scanning electron microscope.

FIG. 2A is a diagram showing an example of a magnetic domain structure specific to a soft magnetic material without a strain.

FIG. 2B is a diagram showing an example of a magnetic domain structure specific to a soft magnetic material with a strain.

FIG. 3A is a diagram showing a positional relationship between pixels in an acquired image.

FIG. 3B is a diagram showing a magnetic domain image and a magnetization amount gradient image that are respectively X and Y components.

FIG. 3C is a diagram showing a magnetic domain image and a magnetization amount gradient image that are respectively X and Y components.

FIG. 4 is a diagram showing an example of a screen of a display device in a scanning electron microscope.

FIG. 5 is a diagram showing another example of the screen of the display device in the scanning electron microscope.

FIG. 6A is a diagram showing a relationship between a scanning electron beam position and an analysis item in creation of a magnetization amount gradient image.

FIG. 6B is a flowchart showing a data analysis method for each pixel.

DESCRIPTION OF EMBODIMENTS

A basic configuration of an electron microscope will be described with reference to FIGS. 1A and 1B. Here, the electron microscope is a strain measurement device that measures a strain of a magnetic body.

As shown in FIG. 1A, the electron microscope includes a stage (not shown) that fixes a sample 101, an electron source 102 that emits a primary electron beam 104, electron optical systems 105 and 106 that scan the sample 101 while irradiating the sample 101 with the converged primary electron beam 104, objective lenses 107, a spin detector 103 that measures a spin polarization of secondary electrons 108 emitted from the sample 101, and an analysis device 100.

Since it is known that the spin polarization of the secondary electrons 108 is correlated with a magnitude of a magnetization, the magnetization of a surface of the sample 101 can be mapped by plotting a value of the spin polarization of the secondary electrons.

A configuration of the analysis device 100 will be described with reference to FIG. 1C.

The analysis device 100 can be constituted by a general computer and peripheral devices thereof. The analysis device 100 is a computer system that executes a program for analyzing secondary electron spin polarization data. The analysis device 100 includes a processing unit 119, a main storage device 120, an auxiliary storage device 130, and an interface (I/F) 140. These components are connected to an internal bus and can communicate with each other.

The analysis device 100 further includes a display device 150 and an input device 162. The display device 150 and the input device 162 are connected to the internal bus via the interface (I/F) 140. The display device 150 is an output device and is, for example, a LCD display or a projector. The input device 162 is, for example, a touch input device, a pen input device, a mouse, or a combination of all or a part thereof.

The processing unit 119 implements a predetermined function of the analysis device 100 by operating in accordance with a program stored in the main storage device 120. The main storage device 120 is, for example, a volatile storage device, and stores a program executed by the processing unit 119 and data to be referred to. For example, the main storage device 120 stores an analysis program 121 in addition to an operating system. The processing unit 119 analyzes the magnetization and strain of the sample in accordance with the analysis program 121 as will be described later.

The auxiliary storage device 130 is, for example, a nonvolatile storage device, and stores data to be loaded into the main storage device 120. In the example of FIG. 1C, the auxiliary storage device 130 stores a database 131. The configuration shown in FIG. 1C is an example, and the analysis device 100 may include components connected to each other via a network or may include a plurality of computers.

As shown in FIG. 1B, the analysis device 100 analyzes the secondary electron spin polarization data and displays an analysis result in accordance with a scanning signal of the primary electron beam 104. Here, in FIG. 1B, the analysis device 100 displays an X component (horizontal component) mapping image 117 and a Y component (longitudinal component) mapping image 118 of the secondary electron spin polarization (magnetization) captured by the scanning electron microscope.

In FIG. 1B, only one magnetic domain and one magnetic domain wall are indicated by reference numerals 115 and 116, respectively. The magnetic domain 115 is a region where the magnetization is constant. The magnetic domain wall 116 is a boundary region between magnetic domains, and is a region in which a magnetization direction (secondary electron spin polarization) changes greatly locally. The analysis device 100 has a function of deriving a magnetization amount gradient image calculated by a method to be described later from data constituting the mapping images 117 and 118. The analysis device 100 visualizes a strain distribution of the sample from the magnetization amount gradient image.

The secondary electron spin polarization, which is an input signal of the scanning electron microscope for mapping the secondary electron spin polarization, is a vector amount reflecting magnetization, and has a magnitude and a direction. Basically, the direction of the magnetization vector is determined by measuring direction components (X, Y, Z components) in a three-dimensional space. However, in the case of a soft magnetic material such as a steel material, a vertical component (Z component) on the sample surface is fairly small due to magnetostatic energy. Therefore, a behavior of the magnetization can be known by measuring only two components (X and Y components) in the sample surface. Therefore, in the following description, it is assumed that a device capable of acquiring only two spin polarization components is used.

As shown in FIG. 2A, in a soft magnetic material having no strain, from the viewpoint of magnetostatic energy, magnetic charge (hereinafter, referred to as magnetic pole) does not occur even in a magnetic domain wall portion where magnetization rotates. For example, in a 180° magnetic domain wall shown in FIG. 2A (a), magnetization vectors (203 and 204) are rotated by 180° with a magnetic domain wall 202 as a boundary. However, since each of the magnetization vectors is located parallel to the magnetic domain wall 202, no magnetic pole is generated in the magnetic domain wall 202.

Or, in a 90° magnetic domain wall shown in FIG. 2A (b), magnetization vectors (207 and 208) are rotated by 90° with a magnetic domain wall 206 as a boundary. However, since magnitudes of respective components of the magnetization vectors perpendicular to the magnetic domain wall are the same, a magnetization amount flowing into the magnetic domain wall 206 is equal to a magnetization amount flowing out of the magnetic domain wall 206. As a result, no magnetic pole is generated in the magnetic domain wall 206. A typical magnetic domain structure of a soft magnetic material having no strain, which is formed by such a magnetic domain wall, is as shown in FIG. 2A (c), and the following (Equation 1) is established in a magnetization distribution of the sample surface.

$$dP_x/dx + dP_y/dy = 0 \qquad \text{(Equation 1)}$$

Here, X and Y are coordinates in a horizontal direction and a longitudinal direction of a magnetic domain image, respectively, and are present in the sample surface. $P_x$ and $P_y$ are secondary electron spin polarizations corresponding to magnetizations in X and Y directions, respectively.

In contract, in the case where a strain (for example, a polishing strain or the like) is present, magnetic anisotropy is generated, a freedom degree of the magnetization direction is reduced, the magnetization direction is not changed even against the magnetostatic energy, and a magnetic pole may be generated in a magnetic domain wall 215 as shown in FIG. 2B (a). In this case, the Equation (1) may not be satisfied only by two-dimensional components of the sample surface.

For example, in the case of the polishing strain, as shown in FIG. 2B (b), the magnetization is oriented in the direction vertical to the sample surface (Z direction in the lower left coordinate) inside the sample, and the magnetization is oriented in a direction vertical to the magnetic domain wall as shown in FIG. 2B (a) in order to relax the magnetostatic energy on the sample surface. As a result, the magnetization of the surface is linked with the magnetization of the inside to form a reflux structure, thereby forming a so-called closure magnetic domain. As a result, the magnetic domain image captured on the sample surface has a magnetic domain structure in which a magnetic pole is generated in the magnetic domain wall 215 as shown in FIG. 2B (a), and in this case, (Equation 1) is not satisfied in the magnetic domain wall portion. That is, it is possible to detect presence or absence of the strain by using (Equation 1) as an index.

Various methods can be considered for the calculation of (Equation 1) in an actual measurement. For example, when a magnetic domain size is sufficiently larger than a pixel interval, calculation in the following procedure is possible in data ($P_x$ (i, j), $P_y$ (i, j)) of the secondary electron spin polarization of a certain analysis target pixel (i, j).

FIG. 3A shows the positional relationship of pixels used for an analysis.

First, regarding the X component, a difference between secondary electron spin polarization data $P_x$ (i, j) in an analysis target pixel 300 (i, j) and secondary electron spin polarization data ($P_x$ (i−1, j)) in a pixel (for example, (i−1, j) in the case of a pixel 301 adjacent in a negative direction) adjacent to either a positive or negative (301 or 302) direction in the X direction is obtained.

Next, regarding the Y component, a difference between secondary electron spin polarization data $P_y$ (i, j) in the analysis target pixel (i, j) and secondary electron spin polarization data ($P_y$(i, j−1)) in a pixel (for example, (i, j−1) in the case of a pixel 303 adjacent in the negative direction) adjacent to either a positive or negative (303 or 304) direction in the Y direction is obtained. Then, the differences between the two components and the respective adjacent pixels are summed up. In this case, the following (Equation 2) is obtained, and calculation having the same meaning as (Equation 1) is possible.

$$P_x(i,j)-P_x(i-1,j)+P_y(i,j)-P_y(i,j-1)=0 \qquad \text{(Equation 2)}$$

An image obtained by plotting the left side is referred to as a magnetization amount gradient image. By analyzing the magnetization amount gradient image, it is possible to easily determine the presence or absence of the strain. In the creation of the magnetization amount gradient image, data between adjacent pixels may be sequentially calculated based on (Equation 2). That is, even if image acquisition is not completed, it is possible to start an analysis of a part from which data has already been acquired even during scanning. A processing of offset or drift of the spin polarization required at the time of the data processing of a spin SEM in the related art is basically unnecessary, and it is possible to visualize presence or absence of a strain fairly easily.

From a viewpoint of S/N, it is also effective to perform a processing of taking average values of a plurality of adjacent pixels in the calculation of (Equation 2), obtaining a difference between the average values for each of X and Y components, and then adding up the difference. An arithmetic expression in this case is given by the following (Equation 3).

$$(P_x(i+2,j)+P_x(i+1,j))/2-(P_x(i,j)+P_x(i-1,j))/2+(P_y(i,j+2)+P_y(i,j+1))/2-(P_y(i,j)+P_y(i,j-1))/2=0 \qquad \text{(Equation 3)}$$

Regarding a method for taking the average in Equation (3), although calculation of the X component handles only two adjacent pixels in the X direction (the first term and the second term in (Equation 3)) and calculation of the Y component handles only two adjacent pixels in the Y direction (the third term and the fourth term in (Equation 3)), there is no particular limitation thereto. The number of pixels to be averaged and the positional relationship may be variously considered.

In addition, in (Equation 2), when there is a strain, although an absolute value of the left side is not zero, it is unknown whether the value is positive or negative. This may complicate the determination of the presence or absence of the strain. For example, in a gray scale, when the vicinity of zero on the left side, that is, when there is no strain, is set to gray, and it is white or black when there is a strain, discrimination of gray is difficult. It is also effective to calculate and display the absolute value of the left side of (Equation 2) so as to be easily determined when visualized. An arithmetic expression in this case is given by the following (Equation 4).

$$|P_x(i,j)-P_x(i-1,j)+P_y(i,j)-P_y(i,j-1)|=0 \qquad \text{(Equation 4)}$$

When (Equation 4) is satisfied, there is no strain in the material, and when (Equation 4) is not satisfied, there is a strain. Since the left side of (Equation 4) is zero or a positive number, when this item is displayed in gray scale on an image for each pixel, it is easy to determine the presence or absence of the strain.

FIGS. 3B and 3C show examples of the case where the presence or absence of strain is analyzed using the magnetization amount gradient image.

First, FIG. 3B shows a magnetic domain image ($P_x$) of a magnetization X direction component, a magnetic domain image ($P_y$) of a magnetization Y direction component, and a magnetization amount gradient image in an example of a field of view without a strain. In an X and Y component image of the magnetization, the magnitude of the magnetization for each component is shown in gray scale.

The magnetization amount gradient image is obtained by plotting the values on the left side of (Equation 2), and it is assumed that the magnetization amount gradient image has a fairly small value in all pixels in a state where there is no strain. This is because the difference between an inflow and outflow of the magnetization is zero not only in the magnetic domain, but also in the magnetic domain wall portion. Actually, in the field of view of FIG. 3B, a contrast of the gray scale is constant as an intermediate color. From this point of view, it is assumed that the magnetic domain image is in a state where there is no strain.

The field of view of FIG. 3C shows an example in which a portion where slight strain occurs is observed.

Although in the magnetization amount gradient image, the contrast is constant at an intermediate color in most regions, black or white lines are observed in a lower part of the field of view. This indicates a region in which the value of the left side of (Equation 2) greatly changes from zero. Here, a white line indicates a portion where the inflow of magnetization is large, and a black line indicates a portion where the outflow of magnetization is large.

That is, in this field of view, although a flow of the magnetization is closed in the two-dimensional plane in an upper portion of the field of view, it is considered that the magnetization partially flows in/out in a direction vertical to the sample surface in a lower portion of the field of view, and is not closed in the two-dimensional plane. This is because of a magnetization structure in which the magnetostatic energy is partially increased on the sample surface due to the magnetic anisotropy caused by a stress in the material, that is, the presence of strain is suggested.

As described above, in the above embodiment, a strain distribution is derived by detecting the secondary electron spin polarization and calculating the acquired data in adjacent pixels. Hereinafter, embodiments will be described.

First Embodiment

A screen example of the display device 150 in the scanning electron microscope for detecting the secondary electron spin polarization will be described with reference to FIG. 4.

The user can use the input device 162 to designate a processing to be executed by the analysis device 100 from a menu bar 400. The menu bar 400 includes, for example, "A: file" for managing storage, reading, printing, and the like of data, "B: data acquisition" linked to a command for starting or stopping data acquisition, "C: parameter" for setting data acquisition time, the number of pixels, and the like, "D: data analysis" for analyzing acquired data, which are selectable.

Here, when "D: data analysis" is selected, an analysis menu 450 in which analysis items such as (1) magnetization direction analysis, (2) magnetization absolute value analysis, and (3) strain amount analysis can be selected is displayed on the screen. Thereafter, when a target analysis item is selected from the analysis menu 450, the analysis device 100 executes an analysis processing selected in the analysis menu 450.

For example, when "strain amount analysis" is selected, the analysis device 100 displays a screen for acquiring a magnetization amount gradient image 440 in addition to a surface shape image 410, a magnetic domain image (magnetization component image) 420, and a magnetic domain image (magnetization component image) 430 together with a window of a strain amount analysis menu 460. The analysis processing is executed in a state in which such a screen is displayed. In the strain amount analysis menu 460, "a: analysis position specification" for selecting a position to be subjected to a strain analysis from the acquired screen, "b: magnetic domain wall width analysis" for measuring the magnetic domain wall width at the selected position, "c: strain amount calculation" for quantitatively calculating the strain amount from the magnetic domain wall width, and the like can be selected.

In a secondary electron spin polarization image acquisition mode, the analysis device 100 displays the surface shape image 410 by, for example, plotting a total number of detected secondary electrons. The analysis device 100 also generates and displays the magnetic domain image (magnetization component image) 420 and the magnetic domain image (magnetization component image) 430 based on spin polarization data from the spin detector 103. Although the analysis device 100 can acquire a component image in each magnetization direction, for example, a component image in the X direction, the Y direction, and the Z direction, in the example of FIG. 4, the magnetic domain image 420 of the magnetization X component and the magnetic domain image 430 of the magnetization Y component are displayed. In order to ensure S/N, the analysis device 100 may perform processing such as averaging (smoothing) of magnetization component data as necessary.

In creation of the magnetization amount gradient image 440, it is a basic principle to calculate $(dP_x/dx+dP_y/dy)$ on the left side of (Equation 1) based on the secondary electron spin polarization data and plot it on each pixel. However, when the pixel interval is sufficiently smaller than the magnetic domain size, the objective is achieved by approximately obtaining the difference between the adjacent pixels in the X direction for the X component, obtaining the difference between the adjacent pixels in the Y direction for the Y component, and plotting a sum of the difference results in both directions on each pixel. The arithmetic expression in this case is (Equation 2), and it can be determined that there is no strain when (Equation 2) is satisfied and there is strain when (Equation 2) is not satisfied.

In the magnetization amount gradient image 440 created in this manner, the contrast of the gray scale is constant in an intermediate color in a portion where there is no strain. In a region with the strain, a part 442 of the magnetic domain wall is displayed in white, and this indicates a portion where a large amount of magnetization inflows. Similarly, a part 441 of a magnetic domain wall displayed in black is also present in a portion having the strain, and this indicates a portion where the outflow of magnetization is large.

Here, a difference between white and black, that is, a difference between the inflow and the outflow of magnetization does not particularly give information about the strain. That is, the information on the direction and magnitude of the stress does not indicate the difference between black and white, and both of them merely show regions having a strain.

The above four images can be partially displayed by calculating already acquired data even while the scanning electron beam sequentially scans the field of view. That is, in the calculation in (Equation 2), since the processing of the offset of the spin polarization and the drift necessary at the time of the data processing of the spin SEM is not necessary, unlike the data analysis in the spin SEM image in the related art, it is not necessary to wait until one image is captured.

After the presence or absence of the strain is visualized by the magnetization amount gradient image 440, further detailed analysis is performed by specifying an analysis position, acquiring a high-magnification image, and measuring, for example, a magnetic domain wall width. A quantitative analysis of the strain is also possible.

Second Embodiment

A screen example of another display device 150 in the scanning electron microscope for detecting the secondary electron spin polarization will be described with reference to FIG. 5.

In the creation of a magnetization amount gradient image 540 of the second embodiment, (Expression 4) is used. In this case, since brightness and darkness of the gray scale in the magnetization amount gradient image 540 directly correspond to the magnitude of a strain amount, it is easy to visually understand the presence or absence of the strain. That is, magnetic domain walls 541 and 542 at positions with a strain both become white and are always displayed brighter than portions without a strain, and it can be interpreted more easily than the method of displaying a portion with high contrast of black or white as in the first embodiment shown in FIG. 4. A method for providing a certain threshold value and extracting and displaying a position larger than the threshold value as a position having a large strain is also effective.

Third Embodiment

Referring to FIG. 6A, a relationship between a scanning electron beam position and an analysis item in creation of a magnetization amount gradient image is shown.

The number of pixels of the two-dimensional image to be acquired is set to m in the X direction and n in the Y direction, and coordinates of an upper left corner of the image are set to (1, 1) and coordinates of a lower right corner are set to (m, n). At this time, the X coordinate and the Y coordinate of the position in the field of view of the scanning electron beam are set to i and j, respectively. Although $P_x$ and $P_y$ of the secondary electron spin polarization data are sequentially acquired at each scanning point, $P_x(i, j)-P_x(i-1, j)$ is calculated for the X component and $P_y(i, j)-P_y(i, j-1)$ is calculated for the Y component while acquiring $P_x$ and $P_y$. Then, it is possible to sequentially create the magnetization amount gradient image by displaying a sum of the calculation result or displaying an absolute value of the result of the sum.

Here, when i=1 or j=1, the above calculation is not established. Therefore, when a size of the magnetic domain image to be acquired is m pixels in the X direction and n pixels in the Y direction, a size of the magnetization amount gradient image is m−1 pixels in the X direction and n−1 pixels in the Y direction.

A data analysis method for each pixel will be described with reference to a flowchart in FIG. 6B.

First, the scanning electron beam moves and a position to be analyzed is determined (S610). Here, the coordinates are (i, j).

At this point, the sample 101 is irradiated with the primary electron beam 104, and the secondary electrons 108 are emitted and collected and transferred to the spin detector 103. A signal from the spin detector 103 is transmitted to the input device 162 of the analysis device 100 (S620).

Then, the spin polarization ($P_x$, $P_y$) is analyzed in the processing unit 119 (S630). The result is sent to the main storage device 120 of the analysis device together with the pixel number (i, j) (S640).

Then, at the same time, already stored $P_x(i-1, j)$ and $P_y(i, j-1)$ are read from the main storage device 120 (S650).

Next, the processing unit 119 calculates $P_x(i, j)-P_x(i-1, j)+P_y(i, j)-P_y(i, j-1)$ (S660).

Next, the calculation result is sent to the main storage device 120 of the analysis device 100 together with the pixel number (i, j) (S670).

After the processing of converting the gray scale to a gray scale level or the like, the gray scale level is plotted on coordinates (i, j) of the magnetization amount gradient image (S680).

Then, the scanning electron beam moves to the next coordinate (i+1, j) and repeats the processing.

The scanning electron microscope according to the above embodiments includes a spin detector that measures a spin polarization degree of secondary electrons emitted from a sample and an analysis device that analyzes measurement data of the spin detector. The analysis device calculates a differential value of each spin polarization component or a difference between adjacent pixels in the measurement data. Therefore, the strain in the sample is evaluated.

According to the above embodiments, it is possible to analyze the strain with high accuracy in the soft magnetic material. For example, when a strain occurs in the sample and a change occurs in an atomic interval, the magnetic anisotropy changes in that portion. It is known that the magnetic anisotropy greatly changes even when the strain is at a level of $10^{-6}$. Therefore, when the strain occurs, the magnetic anisotropy at that portion changes, and the magnetization distribution can be examined in detail and easily using spatial resolution of the scanning electron microscope.

REFERENCE SIGNS LIST

100: analysis device
101: sample
102: electron source
103: spin polarization detector
104: primary electron beam
105: electron optical system
106: electron optical system
107: objective lens
108: secondary electron
115: magnetic domain
116: magnetic domain wall
117: magnetization X component magnetic domain image
118: magnetization Y component magnetic domain image
119: processing unit
120: main storage device
121: analysis program
130: auxiliary storage device
131: database
140: interface
150: display device
162: input device

The invention claimed is:

1. A scanning electron microscope for evaluating a strain in a sample, the scanning electron microscope comprising:
   a spin detector configured to measure secondary electron spin polarization of secondary electrons emitted from the sample; and
   an analysis device configured to analyze secondary electron spin polarization data measured by the spin detector, wherein
   the analysis device evaluates the strain in the sample by calculating a difference in the secondary electron spin polarization data of adjacent pixels.

2. The scanning electron microscope according to claim 1, wherein
   the analysis device is configured to
      individually analyze two orthogonal components of the secondary electron spin polarization,
      calculate a difference in the secondary electron spin polarization data of adjacent pixels in each component, and
      evaluate the strain in the sample by adding up calculation results of the respective components.

3. The scanning electron microscope according to claim 2, wherein
   the analysis device evaluates the strain in the sample by calculating an absolute value of a result obtained by adding up the calculation results of the respective components.

4. The scanning electron microscope according to claim 2, wherein
   the analysis device is configured to
      detect an X component and a Y component in which the secondary electron spin polarization has an X direction and a Y direction in a sample surface of the sample, obtain, for the X component, a difference between data in an analysis target pixel and data in an adjacent pixel in a positive or negative direction in the X direction, obtain, for the Y component, a difference between data in an analysis target pixel and data in an adjacent pixel in a positive or negative direction in the Y direction, and evaluate the strain in the sample by adding calculation results of the X component and the Y component.

5. The scanning electron microscope according to claim 2, wherein the analysis device is configured to detect an X component and a Y component in which the secondary electron spin polarization has an X direction and a Y direction in a sample surface of the sample, and evaluate, when the X component and the Y component of the secondary electron spin polarization are described as $P_x$ and $P_y$, respectively, the strain in the sample by obtaining a value of $dP_x/dx+dP_y/dy$, the value being an item obtained by adding a result of spatial differentiation of the X component and the Y component in the X direction and the Y direction for each of the X component and the Y component.

6. The scanning electron microscope according to claim 2, wherein the analysis device evaluates the strain in the sample by visualizing the calculation results of respective components according to a scanning electron beam position of a scanning electron beam.

7. The scanning electron microscope according to claim 6, wherein the analysis device performs calculation during scanning by the scanning electron beam, and sequentially visualizes the calculation results of the respective components.

8. The scanning electron microscope according to claim 6, wherein the analysis device includes a display device, and the visualization is performed by displaying the calculation results of the respective components on the display device.

9. The scanning electron microscope according to claim 8, wherein the analysis device displays a region in which the calculation results are larger than a predetermined threshold value as a region having the strain on the display device.

10. The scanning electron microscope according to claim 1, wherein the analysis device is configured to individually analyze two orthogonal components of the secondary electron spin polarization, calculate average values in the secondary electron spin polarization data of adjacent pixels in each component, calculate a difference between the average values in the secondary electron spin polarization data of adjacent pixels in each component, and evaluate the strain in the sample by adding up calculation results of the respective components.

11. A scanning electron microscope for evaluating a strain in a sample, the scanning electron microscope comprising:

a spin detector configured to measure secondary electron spin polarization of secondary electrons emitted from the sample; and an analysis device configured to analyze secondary electron spin polarization data measured by the spin detector, wherein the analysis device is configured to detect at least two orthogonal components of the secondary electron spin polarization, and evaluate the strain in the sample by calculating a differential value in each component.

12. The scanning electron microscope according to claim 11, wherein the analysis device is configured to detect an X component and a Y component in which the secondary electron spin polarization has an X direction and a Y direction in a sample surface of the sample, and evaluate the strain in the sample by calculating differential values of the X component and the Y component, respectively.

13. The scanning electron microscope according to claim 12, wherein the analysis device evaluates, when the X component and the Y component of the secondary electron spin polarization are described as $P_x$ and $P_y$, respectively, the strain in the sample by obtaining a value of $dP_x/dx+dP_y/dy$, the value being an item obtained by adding a result of spatial differentiation of the X component and the Y component in the X direction and the Y direction for each of the X component and the Y component.

* * * * *